US00PP16654P3

(12) United States Plant Patent
McLean

(10) Patent No.: US PP16,654 P3
(45) Date of Patent: Jun. 13, 2006

(54) APPLE TREE NAMED 'MC38'

(50) Latin Name: *Malus domestica*
Varietal Denomination: MC38

(75) Inventor: Allan D. McLean, Harcourt North (AU)

(73) Assignee: A.D. McLean Investments Pty. Ltd., Harcourt (AU)

( * ) Notice: Subject to any disclaimer, the term of this patent is extended or adjusted under 35 U.S.C. 154(b) by 0 days.

(21) Appl. No.: 10/660,458

(22) Filed: Sep. 9, 2003

(65) Prior Publication Data

US 2005/0120446 P1 Jun. 2, 2005

Related U.S. Application Data

(63) Continuation of application No. 10/081,731, filed on Feb. 21, 2002, now abandoned.

(51) Int. Cl.
*A01H 5/00* (2006.01)

(52) U.S. Cl. ..... Plt./161
(58) Field of Classification Search ..... Plt./161
See application file for complete search history.

*Primary Examiner*—Bruce R. Campell
*Assistant Examiner*—S. B. McCormick-Ewoldt
(74) *Attorney, Agent, or Firm*—Klarquist Sparkman, LLP

(57) ABSTRACT

A new apple variety distinguished by a spherical fruit shape, late fruit maturity, full-bodied flavor, and extensive striped overcolor.

3 Drawing Sheets

Latin name of genus and species: *Malus domestica* 'MC38'.

RELATED APPLICATION DATA

This application claims priority to U.S. patent application Ser. No. 10/081,731, filed Feb. 21, 2002, entitled, "Apple Tree Named 'MC 38'", by Allan D. McLean, which is hereby incorporated by reference.

SUMMARY

The present invention relates to a new and distinct variety of apple tree named 'MC38,' which was discovered as a chance seedling growing among a uniform block of Pink Lady® 'Cripps Pink' variety (U.S. Plant Pat. No. 7,880) apple trees in a cultivated area of Harcourt, Australia.

The 'MC38' variety is distinguished from other apple varieties due to the following unique combination of characteristics: the fruit is uniformly round, almost spherical, and more red in color than 'Cripps Pink'; the fruit matures later than 'Cripps Pink' and Sundowner® 'Cripps Red' variety (patent pending); the fruit has a higher firmness rating than 'Cripps Pink'.

Asexual reproduction of this new variety was performed in Harcourt, Australia, by grafting and budding onto rootstock shows that the foregoing and all other characteristics and distinctions come true to form and are established and transmitted through succeeding propagations.

The following detailed description concerns the original chance seedling, discovered in 1999, and progeny first asexually propagated in 1999. The original chance seedling and progeny have been observed growing in a controlled area of Harcourt, Australia, and the first observed fruiting of the tree occurred in 1999.

Certain characteristics of this variety, such as growth and color, may change with changing environmental conditions (e.g., light, temperature, moisture), nutrient availability, or other factors. Color descriptions and other terminology are used in accordance with their ordinary dictionary descriptions, unless the context clearly indicates otherwise.

Figure 1:
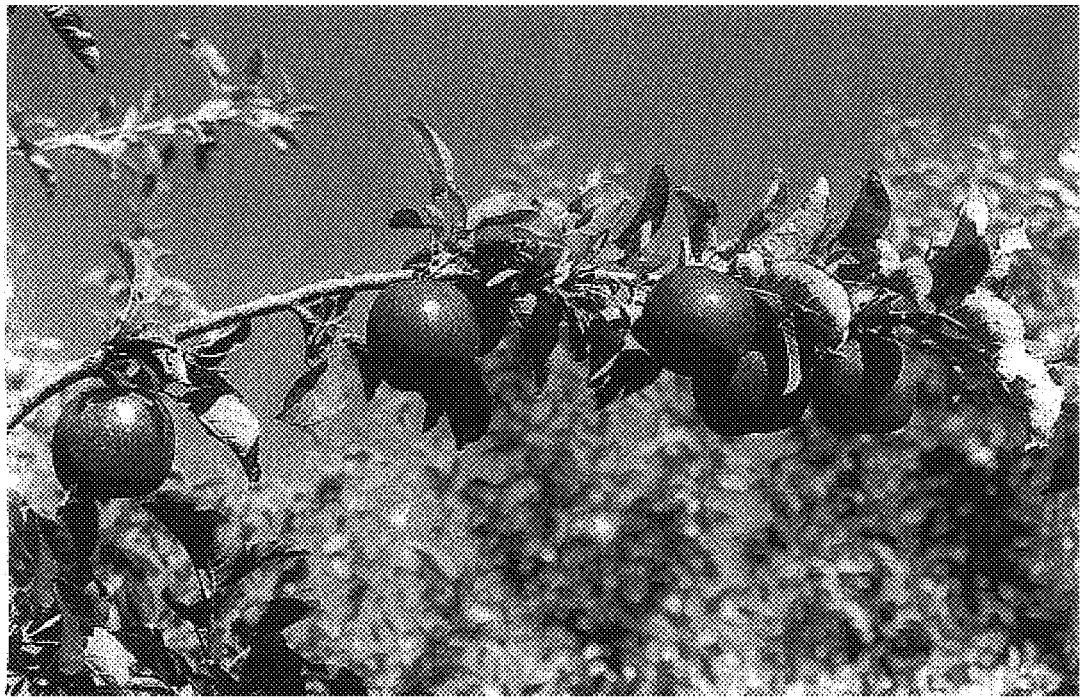
FIG. 1 shows a branch of 'MC38' laden with fruit.
Figure 2:
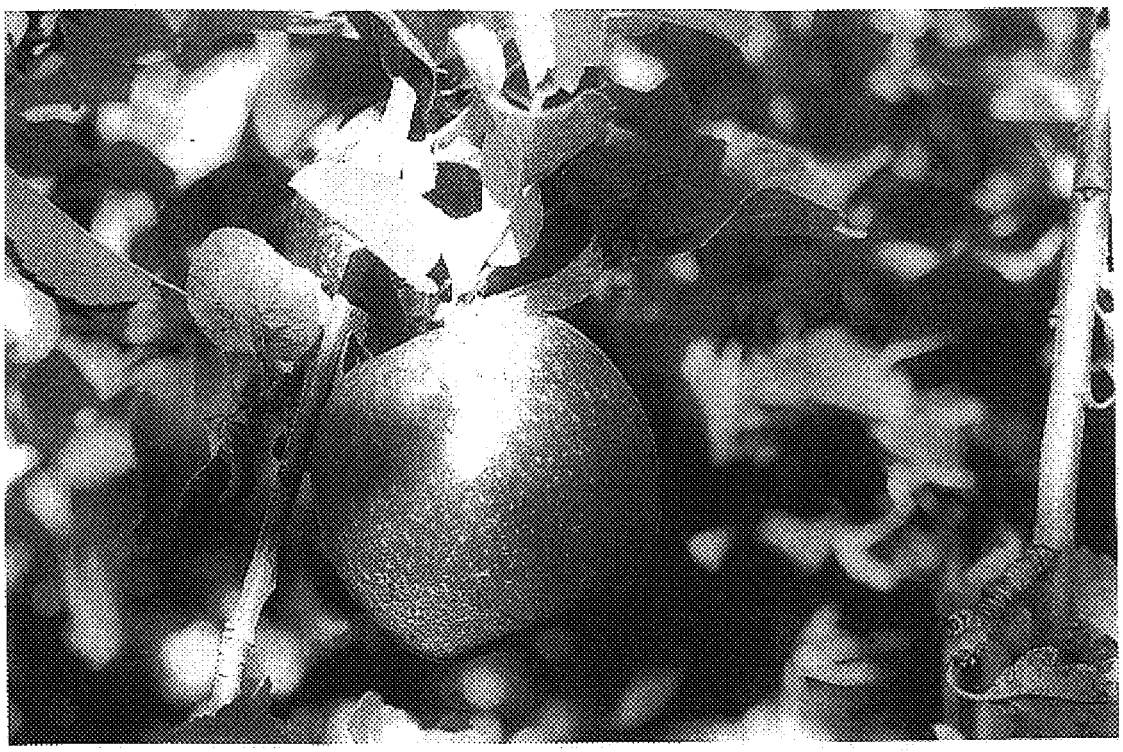
FIG. 2 is a close-up view of fruit, a branch, and leaves of 'MC38.'
Figure 3:
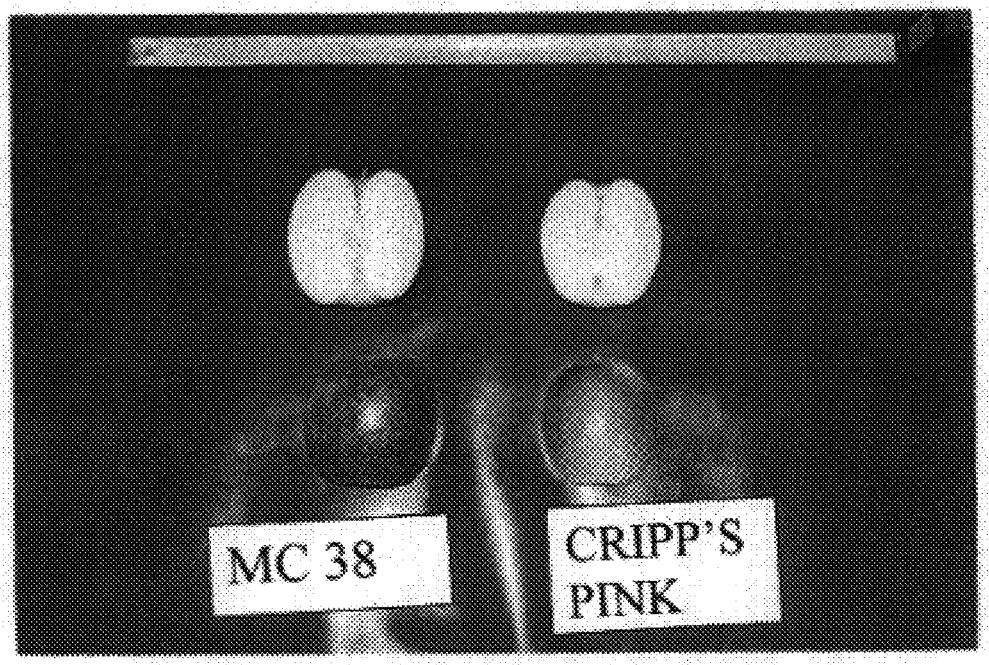
FIG. 3 is a comparison of fruit from 'MC38' and from 'Cripps Pink.'

The colors of this illustration may vary with lighting conditions and, therefore, color characteristics of this new variety should be determined with reference to the observations described herein, rather than from these illustrations alone. Color designations are made with reference to The Royal Horticultural Society (R.H.S.) Colour Chart.

DETAILED DESCRIPTION

The following detailed description of the 'MC38' variety is based on the originally identified tree and asexually reproduced progeny, growing in Harcourt, Australia.

Species: *Malus domestica.*

Parentage: Unknown. Seed parent believed to be 'Cripps Pink.'

Tree: Observed trees were 2–3 years of age growing on MM-106 rootstock (unpatented) in Harcourt, Australia.

*Vigor.*—Moderate. A sample of ten (10) trees grew an average of 46.5 cm per year during the 2000/2001 and 2001/2002 growing seasons. Tree trunk diameter on a sample of ten (10) trees was 29.7 mm at a height of 30 cm above ground level. On a sample of ten (10) trees, tree canopy diameter at a height of 1.2 m was about 1.8 m at the widest point.

*Overall shape.*—Erect, but observed tree spreading through artificial means; young trees strongly apically dominant.

*Trunk bark texture.*—Smooth.

*Trunk bark color.*—Greyed-orange RHS 177A.

*Patches or other markings.*—Prominent lenticel spotting.

*Primary branches.*—Slender; branches emerge at an angle of about 70 to 80 degrees; exemplary two year old primary branches have been observed to have a caliper of about 14 to 15 mm.

*Branch color.*—One-year old branches are greyed-purple (RHS 187A) in color, while older branches are greyed-orange (RHS 166A) in color.

*Branch pubescence.*—Absent.

*Branch lenticels.*—Medium density, approximately 4 to 5 per square centimeter; oblong in shape; cream colored; and typically 1.0 to 1.5 mm long.

*Internodes.*—Average internode length is about 20 to 35 cm for a two-year old shoot.

*Bearing.*—Annual.

*Hardiness.*—Comparable to 'Cripps Red.'

*Disease resistance.*—Susceptible to Black Spot similar to 'Cripps Red' Moderately tolerant to Powdery Mildew. In an observed sampling 'Cripps Red' had Powdery Mildew infection on three to five percent of the leaves while 'MC 38' leaves in a comparison sample showed no infection.

Pedicel:

*Length.*—20 mm.

*Diameter.*—1.14 mm.

*Color.*—Green (RHS 138D).

Peduncle:

*Length.*—4.5–5.5 mm.

*Diameter.*—3–4 mm.

*Color.*—Green (RHS 140D).

Leaves:

*Texture.*—Thin and leathery.

*Sheen.*—Dull.

*Length.*—64.2 mm (average measurement from ten typical leaves).

*Width.*—44.3 mm (average measurement from ten typical leaves).

*Petiole.*—About 26.2 mm long and 1.3 mm in diameter; color is strong red at base fading to green at the top.

*Margin.*—Serrate.

*Tip shape.*—Acute.

*Stipules.*—About two stipules are present; very small and oppositely arranged; red in color; ovate shape with an obvate tip; less than 1 to 2 mm in length.

*Leaf color.*—Upper leaf surface: dark green, (RHS 139A). Lower leaf surface: light green, (RHS 147C). Vein: very light green, (RHS 157A).

*Pubescence.*—Light pubescence on underside of leaf.

Flowers:

*Size.*—Large, sample of 100 flowers averaged 50.6 mm. A particular flower was approximately 54 mm in diameter.

*Shape.*—Ovoid to round.

*Color.*—Unopened bud: red (RHS 47B). Flower — upper petal surface: pink (RHS 66C). Flower — lower petal surface: pink (RHS 66C).

*Petals.*—About five petals per flower. Shape: ovate to oblong, length greater than width (typically 17 mm long and 13 mm wide). Apex-rounded (U-shaped). Base: slightly acuminate.

*Bud length.*—10 mm.

*Bud diameter.*—8.5 mm.

Reproductive organs:

*Stamen.*—20 per flower; each stamen is 8.6 to 10.1 mm long and cream/white in color (RHS 155D). Arranged in a straight row.

*Anthers.*—Cream (RHS 158A), just as flower opened.

*Pistil.*—Stigma: About 5 mm long. Style: 5 in number; yellow/green (RHS 154D).

*Sepals.*—About 9–10 mm long and 4 mm wide (at base); green (RHS 141D) with red/purple (RHS 59A) tinged tip.

*Pollen.*—Cream (RHS 158B).

*Fragrance.*—None.

Fruit (from unthinned trees):

*Size.*—Medium to large, compared to 'Cripps Pink'; average diameter of 72.7 mm for 10 typical 'MC38' apples.

*Shape.*—Symmetrical and spherical; no ribbing; no lobes observed at calyx.

*Cavity.*—Deep.

*Basin.*—Medium wide; average width of 25.2 mm for 10 typical 'MC38' apples.

*Pubescence.*—None.

*Stem.*—Short; average length of 19.5 mm and diameter of 1.92 mm for 10 typical 'MC38' apples; green in color with red stripes.

*Locules.*—About five in number; open; seed free from carpel wall.

*Skin.*—Thick; glossy when polished; fruit does not get waxy in storage.

*Lenticels.*—Low density, about 4 to 6 per square centimeter; conspicuous; cream-white in color.

*Color.*—General color effect: solid striped red overcolor (RHS 53A) that is very conspicuous; background color is yellow-green (RHS 145A). Ground color: does not change greatly as fruit matures. Russetting: none present.

Ten typical apples of the 'M38' and of the 'Cripps Pink' cultivars from trees growing near to one another, were obtained on Apr. 7, 2000, and tested for certain properties. The averages of these properties are set forth in Table 1 below and were as follows:

TABLE 1

| | 'MC 38' | 'Cripps Pink' | 'Cripps Red' |
|---|---|---|---|
| Firmness (pressure, kg/km$^2$) | 9.2 | 8.8 | 8.9 |
| Starch Index On Scale of 1 (high starch) to 6 (low starch) | 1.0 | 1.0 | 1.0 |
| Soluable Solids (in percent) | 11.1 | 13.5 | 12.4 |
| Red Color Rating On a scale of 1 (low) to 5 (high) | 4.5 | 0.7 | 0.7 |

A sample of 10 fruit showed all 10 having a 1.0 starch index.

*Flavor.*—Tart and full-bodied, quantified at about 11.1 Brix.

*Juiciness.*—Moderately juicy.

*Flesh color.*—White (RHS 155A).

*Aroma.*—Moderate aroma.

*Core.*—Diameter at widest point is about 25.9 mm, compared to an overall fruit diameter of about 72.7 mm; shape is horizontal and oblong.

*Pollination.*—Not a self-pollinator. 'Royal Gala' is an example of another apple variety and which is a suitable pollinator.

*Seed.*—About 0 to 2 seeds per cell; elongated in shape; seeds average about 7.82 mm long and 4.86 mm wide; brown in color (RHS greyed-orange group 175A).

*Fruit production.*—First picking date in the 2000 harvest in Harcourt, Australia, was about April 7, and last picking date was about April 28.

*Storage.*—Fruit remains fresh at room temperature for 21 days, and can be stored up to four months in cold storage (34° F.).

*Usage.*—Eating.

We claim:

1. A new and distinct variety of apple tree, substantially as herein shown and described.

* * * * *